United States Patent [19]
Klein et al.

[11] Patent Number: 5,967,777
[45] Date of Patent: Oct. 19, 1999

[54] SURGICAL TEMPLATE ASSEMBLY AND METHOD FOR DRILLING AND INSTALLING DENTAL IMPLANTS

[76] Inventors: Michael Klein, 564 Church Ave., Woodmere, N.Y. 11598; Michael E. Abrams, 6 Diana Cir., Roslyn, N.Y. 11576; Richard J. Manno, 6 Scott Ct., Fort Salonga, N.Y. 11768

[21] Appl. No.: 08/977,324

[22] Filed: Nov. 24, 1997

[51] Int. Cl.⁶ .................. A61C 8/00; A61B 6/14
[52] U.S. Cl. .................. 433/75; 433/76
[58] Field of Search .................. 433/75, 76, 173, 433/213, 214, 215; 606/96, 97

[56] References Cited

U.S. PATENT DOCUMENTS

| | | |
|---|---|---|
| 4,160,322 | 7/1979 | Frazier . |
| 4,324,546 | 4/1982 | Heitlinger et al. . |
| 4,325,373 | 4/1982 | Slivenko et al. .................. 453/176 |
| 4,837,732 | 6/1989 | Brandestini et al. . |
| 5,011,405 | 4/1991 | Lemchen . |
| 5,015,183 | 5/1991 | Fenick .................. 433/76 |
| 5,133,660 | 7/1992 | Fenick .................. 433/76 |
| 5,209,659 | 5/1993 | Friedman et al. . |
| 5,236,432 | 8/1993 | Matsen, III et al. . |
| 5,320,529 | 6/1994 | Pompa .................. 433/76 |
| 5,343,391 | 8/1994 | Mushabac . |
| 5,368,478 | 11/1994 | Andreiko et al. . |
| 5,452,219 | 9/1995 | Dehoff et al. . |
| 5,556,278 | 9/1996 | Meitner .................. 433/75 |
| 5,613,852 | 3/1997 | Bavitz .................. 433/173 |
| 5,636,986 | 6/1997 | Pezeshkian .................. 433/76 |
| 5,718,579 | 2/1998 | Kennedy .................. 433/75 |
| 5,725,376 | 3/1998 | Poirier .................. 433/75 |
| 5,769,636 | 6/1998 | Di Sario .................. 433/75 |
| 5,800,168 | 9/1998 | Cascione et al. .................. 433/75 |

FOREIGN PATENT DOCUMENTS

WO/94/26199  11/1994  WIPO .................. 433/75

*Primary Examiner*—Ralph A. Lewis
*Attorney, Agent, or Firm*—Galgano & Burke

[57] ABSTRACT

A surgical template and method for drilling osteotomies (e.g., holes in a jawbone) and installing one or more dental implants using a surgical template assembly. The surgical template assembly is provided with one or more drill guides and one or more dental implant guides. The guides are positioned in the surgical template assembly by a computer-driven milling machine interfaced with a computer-generated image of a patient's jawbone and a computer-generated simulation of at least one dental implant so that when the surgical template is placed in the patient's mouth a trajectory of the guides in the surgical template into the patient's jawbone corresponds to a trajectory of the computer-generated simulation of the dental implant into the computer-generated image of the patient's jawbone. Preferably, three fiducial markers, provide positional coordination between the CT scan data, the computer-generated simulation of the dental implant, and the computer-driven milling machine.

20 Claims, 8 Drawing Sheets

SURGICAL TEMPLATE ASSEMBLY AND METHOD FOR DRILLING AND INSTALLING DENTAL IMPLANTS

BACKGROUND OF THE INVENTION

The present invention relates to a surgical template assembly and method for drilling and installing dental implants. More particularly, the invention relates a surgical template assembly and method for precisely drilling and installing dental implants using a surgical template assembly having one or more drill guides and one or more dental implant guides. The guides are located in the surgical template assembly by a computer-driven milling machine interfaced with computer-generated images of a patient's jawbone and a superimposed computer-generated simulation of one or more dental implants so that when the surgical template is placed in the patient's mouth a trajectory of the guides into the patient's jawbone corresponds to a trajectory of the computer-generated simulation of the one or more dental implants into the computer-generated image of the patient's jawbone.

Dental implants are devices which are surgically implanted into the jawbone of a patient in the areas where the patient is missing teeth. These devices mimic the roots of teeth and serve to support prosthetic caps, crowns, bridges or dentures. Dental implants are typically titanium metal-based and are generally cylindrical or screw-shaped in design.

Implants must be placed in a specific position and in alignment to the prospective teeth that they will eventually support. Therefore, the positioning of these dental implants must be precise to enable teeth to be made that will function properly and be esthetic in appearance.

Typically, a dental surgeon, after the gum is moved aside, uses a hand held drill to make a hole/osteotomy in the jawbone at the site that is to receive the dental implant. The hole that is drilled into in the patient's jawbone needs to have a defined trajectory, depth and diameter. These parameters are defined by the anticipated position of the patient's teeth to be replaced and supported by the implant(s), and existing anatomic structures, e.g., jawbone height and width, proximity to nerves, existing tooth roots, and sinus cavities.

It is recommended that a surgical template be used as a guide to assist the surgeon in positioning and angling the dental implant drill during dental implant surgery. However, some surgeons choose not to use a surgical template. Fabrication of a surgical template, which acts as a guide for this drilling procedure, generally includes the following steps:

1) Making a plastic replica of the prospective teeth; and
2) Modifying the plastic replica teeth to allow guidance of the position and angulation of the dental implant drill through the replica teeth. This is accomplished by making hole(s) in the plastic replica teeth in the approximate area where the surgeon anticipates he or she will be placing the implant(s).

If a computed tomography scan (CT scan) is to be taken of the patient's jawbone prior to implant surgery, it is recommended that a CT scan appliance is worn by the patient during the CT scan procedure. However, some surgeons choose to have their patients scanned without the use of a CT scan appliance.

Fabrication of a CT scan appliance generally includes the following steps:

1) Making a plastic replica of the prospective teeth to be supported by dental implants; and 2) Placing radiopaque material in and/or on the plastic replica of the prospective teeth. This can be accomplished by applying a radiopaque paint, e.g., barium sulfate acrylic, to the surface of the replica or drilling a groove along the side of the replica and filling the groove with metallic dental filling material.

Once the CT scan has been taken with the patient wearing the CT scan appliance, the CT scan data is reformatted via software to create various two-dimensional images, e.g., views along a cross-sectional, an axial, and a panoramic reference planes. A suitable software program to reformat the CT scan data is SIM/PLANT, manufactured by Columbia Scientific Inc. of Columbia, Md. The software program enables the surgeon to perform a dental implant simulation directly onto the reformatted CT scan images. In particular, the surgeon can view the position of the patient's jawbone, the dental implant simulation, and the image of the radiopaque material, e.g., the outline of the plastic replica. The CT scan appliance can now be modified, as described above, so that it becomes a surgical template.

At the time of surgery, the surgeon moves the gum away to expose the patient's jawbone. The surgeon then places the surgical template in the patient's mouth and to the best of his or her ability orients and guides the dental implant drill with the use of the surgical template.

In general, the dental implant drill is inserted through the hole in the surgical template and oriented by "eyeballing" the dental implant drill through the hole in the surgical template into the patient's jawbone. This procedure is not precise. The diameter of the holes made in the surgical template are usually much larger than the diameter of the implant drill bit.

In addition, during dental implant surgery the implant drill is manipulated by hand and in an up and down manner by the surgeon. Specifically, the surgeon "eyeballs" the three-dimensional trajectory/angulation of the implant drill bit relative to the surgical template and adjacent anatomic structures as he drills into the jawbone. The trajectory of the drill can be easily changed in an instant which can ruin the procedure. This aforementioned drilling process is fraught with the potential for many drilling errors which can undermine the success and even result in the failure of the overall procedure.

An attempt to increase the accuracy of locating a dental implant in a patient's jawbone is disclosed in U.S. Pat. No. 5,320,529 to Pompa. In particular, Pompa discloses a method of determining dental implant placement position by taking a CT scan of the patient's upper or lower jaw and then fabricating a model of that jaw from the reformatted CT scan data.

The model is made from a clear plastic/acrylic material into which the surgeon then drills a hole by hand. The surgeon then inserts a dental implant replica (a dummy implant) into the hole and inspects the dummy implant position for acceptability by looking at the dummy implant position through the clear model.

A cylinder is then attached to the top of the dummy implant and acrylic is added around the cylinder and on the surface of the jaw model. The acrylic piece with the encased cylinder now becomes a surgical template which rests on top of the patient's jawbone during the actual implant surgery.

Drawbacks with the method disclosed in Pompa include the following:

1) Creating a plastic jaw model from the CT data.
2) Determining the dental implant position manually. For example, by "eyeballing" the prospective implant position, the surgeon, via the use of a hand-held drill, drills a hole into the plastic jaw model. The surgeon then places a dummy implant into that hole.

3) Lack of visualization of the prospective teeth to receive the dental implant support. For example, there is no coordination between prospective tooth position and dental implant position.

4) Transferring the dental implant position to the surgical template by attaching cylinders to the top of dummy implants that were placed into the jawbone model.

Thus, there is a need for a novel surgical template assembly and method which reduces, if not eliminates, the errors associated with the surgeon "eyeballing" the proper position and angulation of the drill during the drilling process of dental implant surgery. Furthermore, the novel surgical template assembly is enhanced by a system of interchangeable components for precisely guiding one or more drill bits, burs, bone taps, countersinks, other bone or soft-tissue drilling components, and the dental implant itself during the dental implant surgical procedure.

SUMMARY OF THE INVENTION

It is therefore an object of the present invention to provide a novel surgical template assembly for more accurately locating and positioning both an implant hole/osteotomy and a dental implant in a jawbone of a patient.

It is another object of the present invention to provide a surgical template assembly having one or more drill guides and one or more dental implant guides which are precisely located via a computer-driven milling machine.

It is still another object of the present invention to provide a surgical template assembly having fiducial markers, e.g., radiopaque markers, for coordination of the surgical template assembly to a computer-driven milling machine, and for coordination of reformatted CT scan data and a computer-generated simulation of one or more dental implants.

It is yet another object of the present invention to provide a surgical template assembly having interchangeable components for precisely guiding one or more drill bits and desirably a dental implant during surgery along a predetermined trajectory into the desired implant position in the patient's jawbone.

It is also an object of the present invention to provide a novel dental implant drilling and placement method using such a surgical template assembly.

Certain of the foregoing and related objects are readily obtained according to the present invention in a method for locating a dental implant in a patient's jawbone in which the method comprises the steps of fitting a CT scan appliance to a patient's mouth, obtaining CT scan data of the patient's jawbone and the CT scan appliance, and computer generating an image of the patient's jawbone from the CT scan data and a simulation of a dental implant.

The method also comprises the steps of providing a computer-driven milling machine, supporting the CT scan appliance on the computer-driven milling machine, and drilling a hole in the CT scan appliance to form a surgical template. The computer-driven milling machine is interfaced with the computer-generated simulation of the dental implant so that when the surgical template is refitted in the patient's mouth, a trajectory of the hole in the surgical template into the patient's jawbone corresponds to a trajectory of the corresponding computer-generated simulation of the dental implant into the computer-generated image of the patient's jawbone.

The method further comprises the steps of fitting the surgical template to the patient's mouth, and guiding a drill through the hole in the surgical template and into the patient's jawbone to form a hole in the patient's jawbone.

Preferably, the method further comprises the step of coordinating the CT scan appliance to the computer-driven milling machine. Desirably, the CT scan appliance comprises at least one, and desirably three radiopaque fiducial markers. The fiducial markers provide coordination between the CT scan data, the computer-generated simulation of the dental implant, and the computer-driven milling machine. Advantageously, the computer-driven milling machine comprises a table with tooling locators for interlocking with the CT scan appliance.

Most preferably, the step of guiding a drill through the hole in the surgical template comprises inserting a drill bushing in the hole for guiding the drill. Advantageously, the step of guiding a drill through the hole in the surgical template comprises the step of inserting a master cylinder in the hole in the surgical template and inserting a drill bushing in the master cylinder to form a surgical template assembly.

Also desirably, the method further comprises the step of guiding a dental implant through the hole in the surgical template and into the hole in the patient's jawbone, and advantageously, inserting a master cylinder in the hole in the surgical template and inserting an implant bushing in the master cylinder to form a surgical template assembly.

Certain of the foregoing and related objects are also readily obtained according to the present invention in a method for locating a dental implant in a patient's jawbone in which the method comprises the steps of providing a replica of prospective teeth to be supported by a dental implant, providing a computer-driven milling machine comprising a table, securing the replica to the table, securing at least one fiducial marker to the replica to form a CT scan appliance, and coordinating the at least one fiducial marker to the computer-driven milling machine.

The method also comprises the steps of positioning the CT scan appliance in a patient's mouth, obtaining CT scan data of the patient's jawbone and the at least one fiducial marker, computer generating an image of the patient's jawbone from the CT scan data and a superimposed simulation of a dental implant, resupporting the CT scan appliance to the table in the computer-driven milling machine, drilling, via the computer-driven milling machine, a hole in the CT scan appliance to form a surgical template, the computer-driven milling machine being interfaced with the computer-generated simulation of the dental implant so that when the surgical template is refitted in the patient's mouth, a trajectory of the hole in the surgical template into the patient's jawbone corresponds to a trajectory of the computer-generated simulation of the dental implant into the computer-generated image of the patient's jawbone, the at least one fiducial marker providing positional coordination between the CT scan data, the computer-generated dental implant position, and the computer-driven milling machine.

The method further comprises inserting a master cylinder in the hole in the surgical template, inserting a drill bushing in the master cylinder to form a surgical template assembly, positioning the surgical template assembly in the patient's mouth, and guiding a drill through the drill bushing in the surgical template assembly to provide a hole in the patient's jawbone.

Preferably, the method comprising the steps of removing the drill bushing and inserting an implant bushing in the master cylinder, and guiding a dental implant through the implant bushing in the master cylinder in the surgical template and into the hole in the patient's jawbone.

Certain of the foregoing and related objects are further readily obtained according to the present invention in a method for fabricating a surgical template for use in locating a dental implant in a patient's jawbone in which the method comprises obtaining a CT scan appliance, obtaining computer-generated data of the CT scan appliance and a simulation of a dental implant, supporting the CT scan appliance in a computer-driven milling machine, and drilling, via the computer-driven milling machine, a hole in the CT scan appliance, the computer-driven milling machine being interfaced with the computer-generated simulation of the dental implant so that when the surgical template is refitted in the patient's mouth, a trajectory of the hole into the patient's jawbone corresponds to a trajectory of the computer-generated simulation of the dental implant into the computer-generated image of the patient's jawbone.

Preferably, the CT scan appliance comprises at least one fiducial marker so that the fiducial marker provides positional coordination between the CT scan appliance, the computer-generated simulation of the dental implant, and the computer-driven milling machine.

Desirably, the method further comprises the steps of obtaining CT scan data of the patient's jawbone and the CT scan appliance, and computer generating a simulation of a dental implant.

Certain of the foregoing and related objects are further readily attained according to the present invention in a surgical template positionable in a mouth of a patient for use in locating a dental implant in a patient's jawbone in which the surgical template comprises a replica of the prospective teeth to be implanted. The replica comprises a hole therethrough drilled by a computer-driven milling machine interfaced with a computer-generated image of a patient's jawbone and a computer-generated simulation of a dental implant so that, when the surgical template is placed in the patient's mouth, a trajectory of the hole in the replica into the patient's jawbone corresponds to a trajectory of the computer-generated simulation of the dental implant into the computer-generated image of the patient's jawbone.

BRIEF DESCRIPTION OF THE DRAWINGS

These and other objects and advantages of the present invention will become apparent from the following description of the accompanying drawings, which disclose several embodiments of the present invention. It is to be understood that the drawings are to be used for purposes of illustrations only, and not as a definition of the invention.

In the drawings, wherein similar reference numerals denote similar elements throughout the several views.

DETAILED DESCRIPTION OF THE PREFERRED EMBODIMENTS

Figure 1:
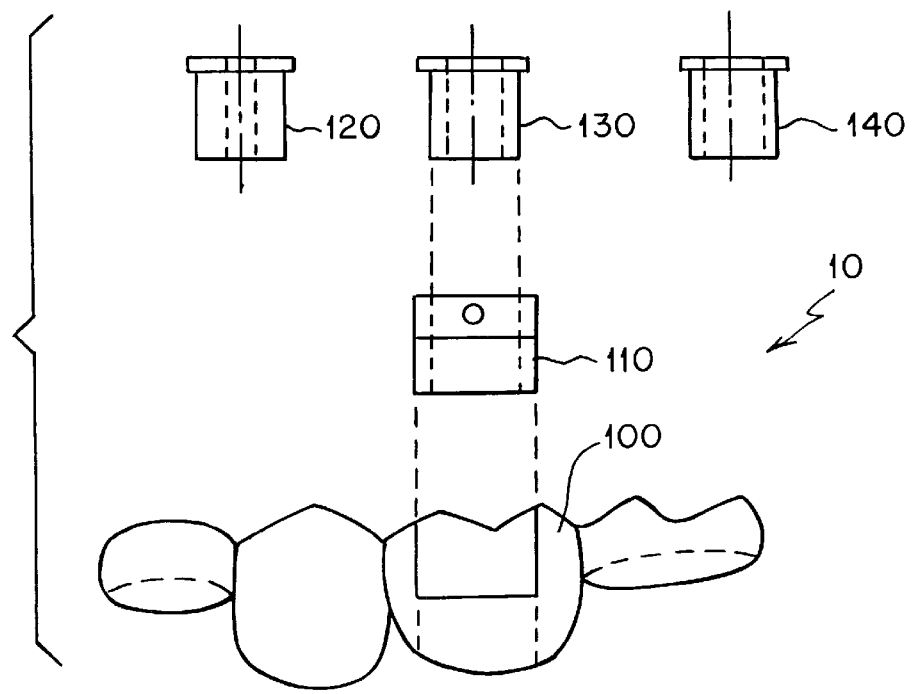
FIG. 1 is an exploded side elevational view of one embodiment of a novel surgical template assembly according to the present invention.
Figure 27:
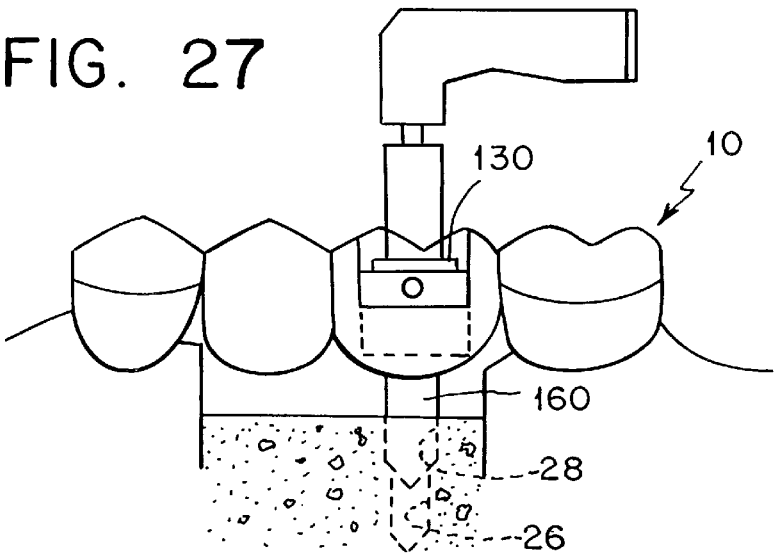
FIG. 27 is a side elevational view of the surgical template assembly shown in FIG. 26 guiding a drill bit for enlarging the pilot hole in the patient's jawbone.
Figure 28:
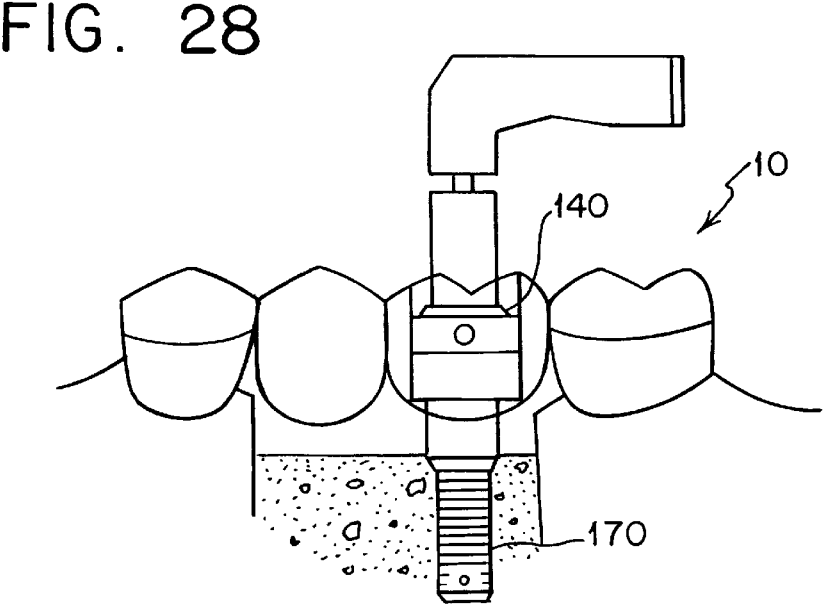
FIG. 28 is a side elevational view of the surgical template assembly shown in FIG. 22 with the implant bushing shown in FIG. 20 for guiding a dental implant into the patient's jawbone.

Referring now in detail to the drawings and, in particular to FIG. 1 thereof, therein illustrated is one embodiment of a novel surgical template assembly 10 according to the present invention for precisely locating and surgically implanting a dental implant 170 (FIG. 28) in the jawbone of a patient. In this illustrated embodiment, surgical template assembly 10 includes a surgical template 100, a master cylinder 110, a first drill bushing 120 for precisely guiding a drill bit for drilling a pilot hole in a patient's jawbone (FIG. 25), a second drill bushing 130 for precisely guiding a drill bit to enlarge the pilot hole (FIG. 27), and an implant bushing 140 for precisely guiding a dental implant into the enlarged hole in the patient's jawbone (FIG. 28).

As will become apparent from the detailed description below, the present invention provides surgical template assembly 10 with both drill and dental implant guides which, when the surgical template assembly is positioned in the patient's mouth, are aligned with and correspond to a trajectory of a computer-generated simulation of one or more dental implant positions superimposed on computer-generated images of the patient's jawbone. The simulated dental implant position and trajectory are interfaced with and transferred to a computer-driven milling machine for positioning the master cylinder, drill bushing and dental implant bushing in the surgical template assembly. Coordinating indicia or fiducial markers are used to interface the computer-generated simulation of the dental implant to a computer-driven milling machine for precisely locating the position and orientation of the drill and implant bushings.

Figure 2:
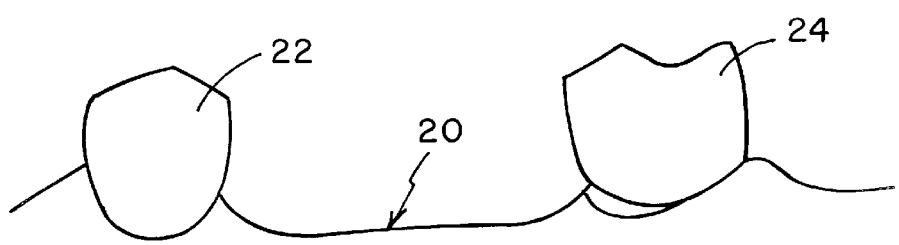
FIG. 2 is a side elevational view of a patient's jaw in which two teeth border a space where teeth are missing.
Figure 3:
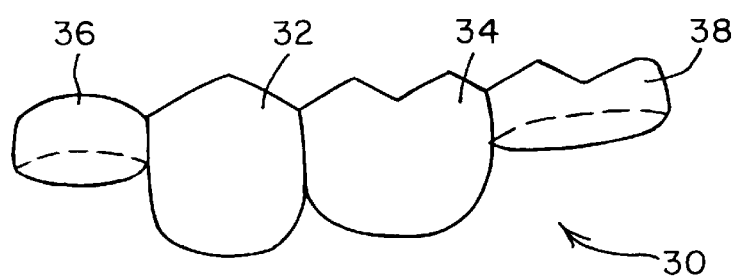
FIG. 3 is a side elevational view of a plastic replica (prospective teeth and anchors) which is positionable in the space where the teeth are missing shown in FIG. 2.

In the fabrication of surgical template assembly 10 initially, diagnostic steps are taken to determine final tooth position for a dental prosthesis. For example, FIG. 2 illustrates a patient's jaw 20 in which two teeth 22 and 24 border a space where teeth are missing. As shown in FIG. 3, a plastic replica 30 comprising teeth 32 and 34 to be implanted is made which demonstrates final tooth position. Preferably, plastic replica 30 comprises anchors 36 and 38 for attaching plastic replica 30 to the patient's teeth 22 and 24 (FIG. 2) bordering the space.

FIGS. 4–8 illustrate the procedure for converting plastic replica 30 (FIG. 3) to a CT scan appliance 80 (FIGS. 7 and 8) so that plastic replica 30 can be coordinated to a computer-driven milling machine 60 (FIG. 10), e.g., a three or five axis computer numerical control (CNC) milling machine, and interfaced with a computer-generated image of the patient's jawbone and superimposed computer-generated simulation of a dental implant.

Figure 10:
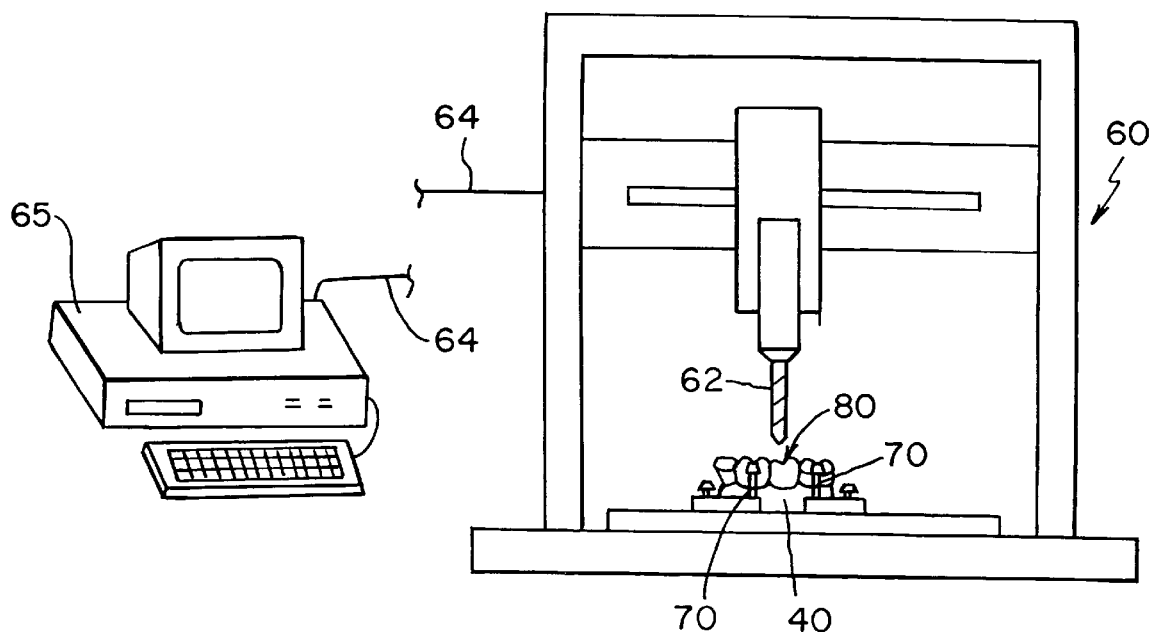
FIG. 10 is a side elevational view of a computer-driven milling machine illustrating the operation of drilling a hole precisely into the CT scan appliance.

A model or support 40 (FIG. 4A) is used to position and support plastic replica 30 (FIG. 4B) on a table 50 (FIGS. 5 and 6) of computer-driven milling machine 60 (FIG. 10). Preferably, model 40 is in the form of the portion of the patient's jaw and soft tissue where the patient is missing teeth. Desirably, model 40 is fabricated from plaster, stone, or other rigid material. As will be explained in greater detail below, the model may be in the form of the complete upper or lower jawbone and soft tissue of the patient. This would be particularly suitable for implanting several dental implants.

Figure 5:
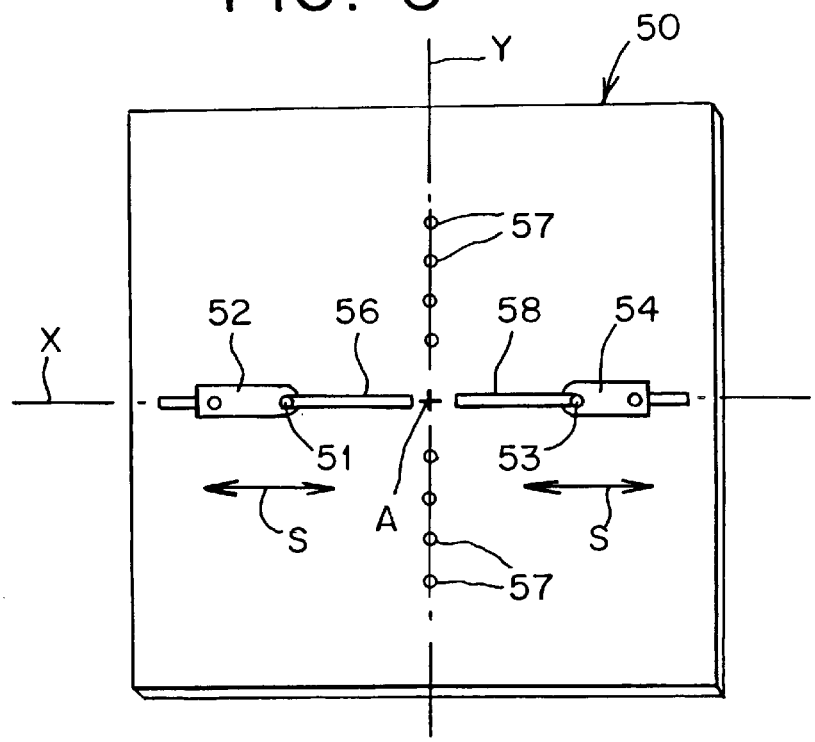
FIG. 5 is a top view of a table used to interface with the computer-driven milling machine (FIG. 10)
Figure 4A:
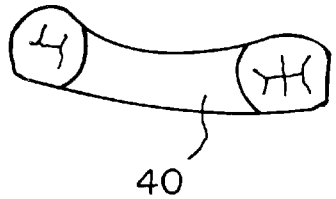
FIG. 4A is a top view of a model for supporting the plastic replica shown in FIG. 3.
Figure 4B:
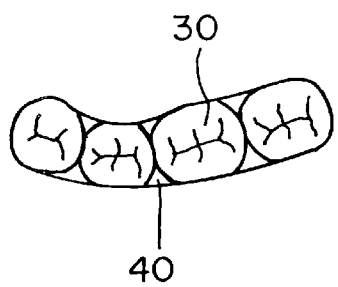
FIG. 4B is a top view of the plastic replica shown in FIG. 3 supported on the model shown in FIG. 4A.

As shown in FIG. 5, table 50 is provided with spaced-apart slidable tooling locators 52 and 54 movable along slots 56 and 58 in the directions of double headed arrows S. Slots 56 and 58 are disposed along a line defining an axis X. Tooling locators 52 and 54 are also provided with vertically extending pins 51 and 53, respectively. In addition, table 50 is provided with a plurality of spaced-apart holes 57 disposed along a line defining an axis Y which is disposed at right angles, i.e., 90 degrees, preferably on both sides of axis X. From the present description, it will be appreciated to those skilled in the art that tooling locators 52 and 54 and holes 57 define orthogonal axes wherein the intersection of the axes define an origin A which may be suitably initialized with and/or coordinated to the drill bit of computer-driven milling machine 60 (FIG. 10), e.g., the starting point or initial value, e.g., X=0, Y=0.

Figure 6:
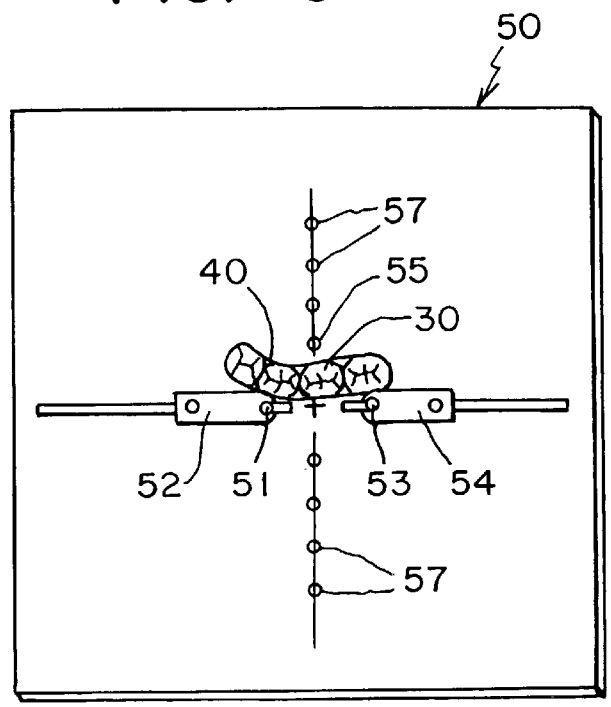
FIG. 6 is a top view of a table shown in FIG. 5, along with the plastic replica shown in FIG. 3 supported on the model shown in FIG. 4.

With model 40 and plastic replica 30 placed on table 50, as shown in FIG. 6, tooling locators 52 and 54 are adjusted so that pins 51 and 53 are positioned adjacent to plastic replica 30. A pin 55 is inserted into one of holes 56 adjacent to plastic replica 30. Pins 51, 53, and 55 are used to position and fix the fiducial markers to plastic replica 30.

Preferably, the three fiducial markers 70 (FIGS. 7 and 8), e.g., radiopaque markers, are hollow and have conical-shaped upper portions. One fiducial marker is placed on each of pins 51, 53, and 55, and attached to plastic replica 30 with acrylic or other suitable adhesive so as to form a CT scan appliance 80. Advantageously, the three fiducial markers 70 are positioned in a plane parallel to table 50, e.g., preferably the fiducial markers are all placed at the same height above table 50. As will become apparent from the following description, CT scan appliance 80 can be removed from model 40 and table 50, and be readily repositioned thereon by sliding fiducial markers 70 over pins 51, 53, and 55.

From the present description, it will be appreciated that model 40 need not be in the form of the patient's teeth so long as it provides a suitable support for the plastic replica of the prospective teeth and coordination of the fiducial markers with the computer-driven milling machine. In addition, the table may be provided solely with a plurality of holes with defined orthogonal axes. From the present description, it will be appreciated by those skilled in the art that the plastic replica can be made of or have embedded therein radiopaque materials, magnetic materials, optical materials, or combinations thereof, so long as the CT scan appliance can be three-dimensionally coordinated to the computer-driven milling machine.

Figure 9A:
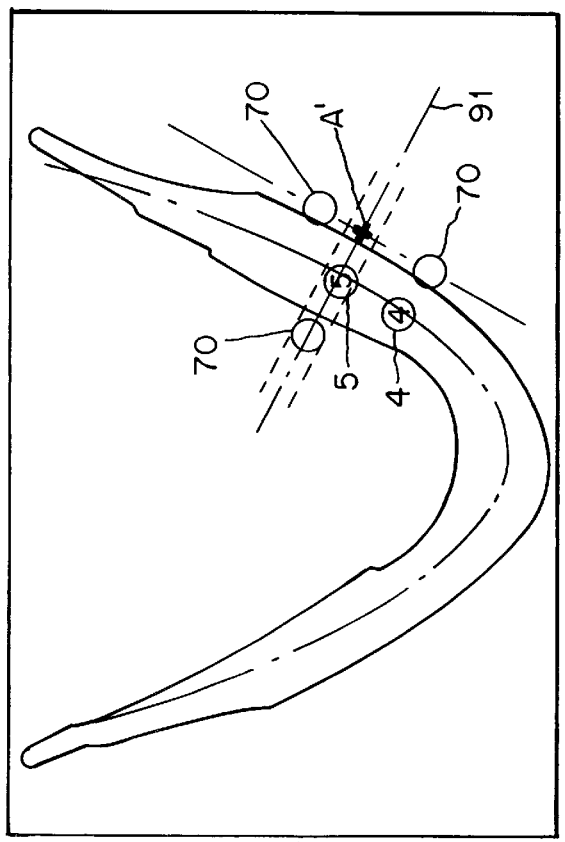
FIGS. 9A–9C are computer-generated images of the patient's jaw and superimposed computer-generated simulation of dental implants.
Figure 9B:
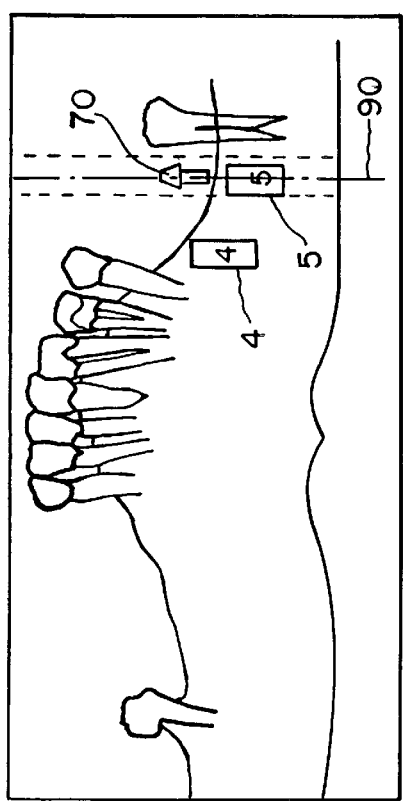
Figure 9C:
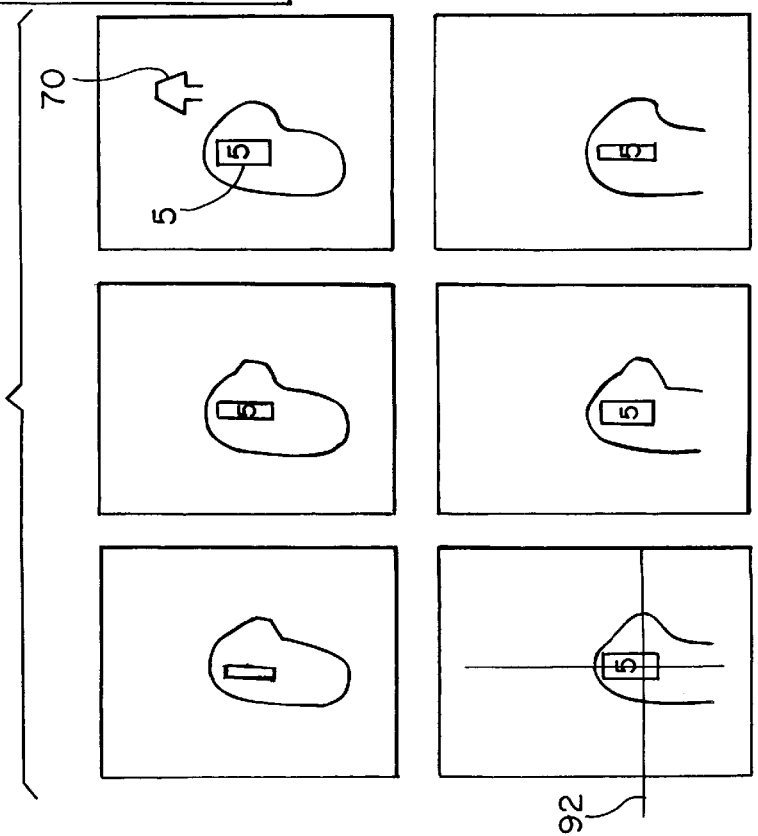
Figure 15:
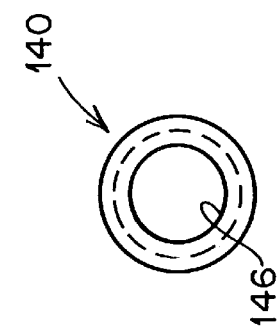
FIGS. 15 and 16 are enlarged top and side elevational views, respectively, of a first drill bushing shown in FIG. 1 for guiding a drill bit for drilling a pilot hole in a patient's jawbone.
Figure 17:
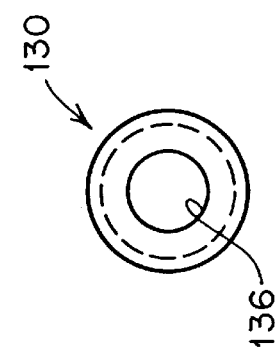
FIGS. 17 and 18 are enlarged top and side elevational views, respectively, of a second drill bushing shown in FIG. 1 for guiding a drill bit for enlarging the pilot hole in a patient's jawbone.
Figure 19:
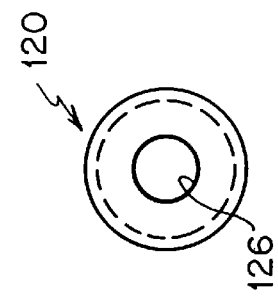
FIGS. 19 and 20 are enlarged top and side elevational views, respectively, of an implant bushing shown in FIG. 1 for guiding a dental implant into a patient's jawbone.
Figure 13:
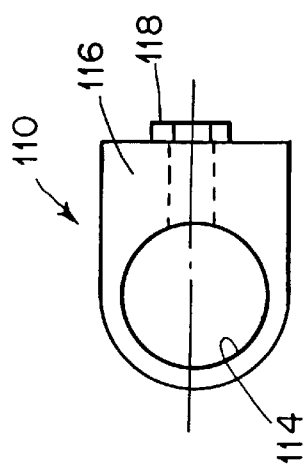
FIGS. 13 and 14 are enlarged top and side elevational views, respectively, of a master cylinder shown in FIG. 1.
Figure 16:
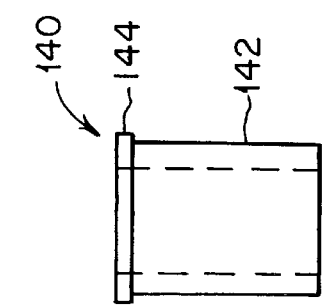
Figure 18:
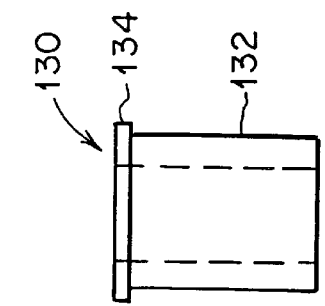
Figure 20:
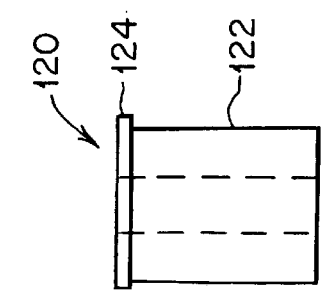
Figure 14:
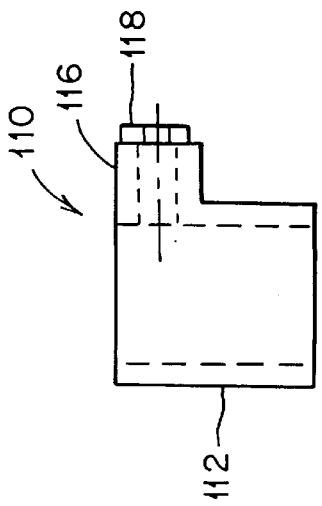

After attaching fiducial markers 70 to plastic replica 30, CT scan appliance 80 is removed, and repositioned in the mouth of the patient during a CT scan procedure of the patient's jawbone and teeth when present. FIGS. 9A–9C illustrate the CT scan data reformatted through a surgical simulation software program and displayed on a computer screen. A suitable surgical simulation software is SIM/PLANT produced and sold by Columbia Scientific, Inc., of Columbia, Md. The software also enables the surgeon to superimpose three-dimensional simulated dental implants 4 and 5.

For example, FIG. 9A is an axial view looking down on the patient's jaw with superimposed simulated dental implants 4 and 5 and visible fiducial markers 70, FIG. 9B is a frontal panoramic view with simulated dental implants 4 and 5 and visible fiducial marker 70, and FIG. 9C are cross-sectional views of the patient's jaw, spaced 1-mm apart from each other, of the jaw portion containing simulated dental implant 5.

Suitable software coordinates the software program, e.g., the simulated dental implant position and angulation, to the computer-driven milling machine 60 by, e.g., extrapolating the position and angulation for the computer-driven milling machine based on measurements relative to the plane of the fiducial markers. In addition, an origin A' (FIG. 9A) is readily coordinated to origin A on the table of the computer-driven milling machine 60. Alternatively, the software program also provides defined three-dimensional axes 90, 91 and 92 (FIG. 9) which correspond to simulated dental implant 5 and which are suitably coordinated three-dimensionally relative to the fiducial markers 70, and thus, to computer-driven milling machine 60.

Figure 11:
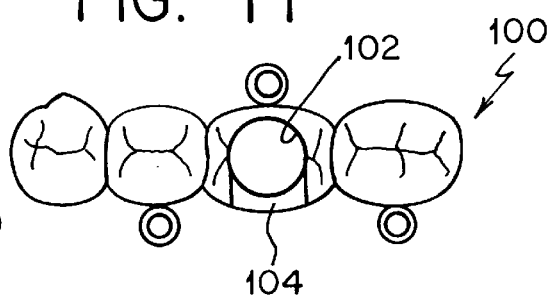
FIG. 11 is an enlarged top view of the surgical template shown in FIG. 1.
Figure 7:
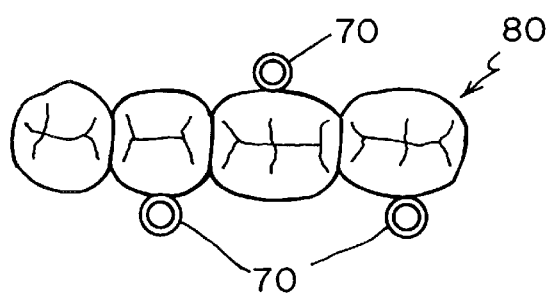
FIG. 7 is a top view of a plastic replica with attached radiopaque fiducial markers so as to form a CT scan appliance.
Figure 12:
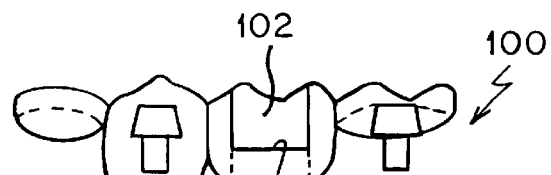
FIG. 12 is a side elevational view of the surgical template shown in FIG. 11.
Figure 8:
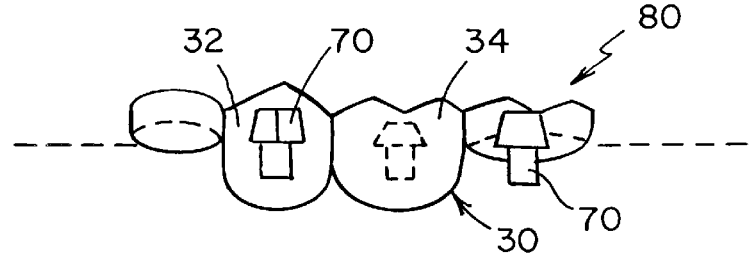
FIG. 8 is a side elevational view of the CT scan appliance shown in FIG. 7.

Next, CT scan appliance 80 is repositioned on model 40 and table 50, i.e., fiducial markers 70 are repositioned on pins 51, 53, and 55, as shown in FIG. 10, and the surgical simulation software is interfaced with computer-driven milling machine 60 via a wire or computer cable 64 attached to a computer 65 to send three-dimensional positioning data regarding the position and angulation of simulated dental implant 5 to computer-driven milling machine 60. A drill bit 62 of computer-driven milling machine 60 accurately drills a hole 102 (best seen in FIG. 11), corresponding to the defined three-dimensional trajectory of simulated dental implant 5 into CT scan appliance 80 (FIGS. 7 and 8) to form a surgical template 100 shown in FIGS. 11 and 12. The forward or upper portion of hole 102 of surgical template 100 is desirably removed in such a fashion as to provide a cutout 104 for receiving master cylinder 110, as will be explained below.

FIGS. 13–20 show various interchangeable components that fit into surgical template 100 (FIGS. 11 and 12) to form surgical template assembly 10 (FIG. 1). For example, in this illustrated embodiment, the components include master cylinder 110, first drill bushing 120, second drill bushing 130, and implant bushing 140. Master cylinder 110 comprises a generally hollow cylindrical body 112 having an outer diameter which is sized to be received in hole 102 of surgical template 100 and an inner axial bore 114 as explained below, which is sized for holding the various guide and dental implant bushings in position. Outwardly extending from the top portion of master cylinder 110 is a flange 116 having a setscrew 118.

Bushings 120, 130, and 140 comprise generally hollow cylindrical bodies 122, 132, and 142, with upper outwardly extending rims 124, 134, and 144, respectively. The outer diameter of bushings 120, 130, and 140 are sized to be received in axial bore 114 of master cylinder 110. As seen in FIGS. 15–20, first bushing 120 has an axial bore 126, second drill bushing 130 has an axial bore 136 which is larger than axial bore 126 of first drill bushing 120, and implant bushing 140 has an axial bore 146 which is larger than axial bore 136 of second drill bushing 130 for guiding a dental implant. Flange 116 of master cylinder 110 is provided with a threaded hole in which is receivable setscrew 118 to releasably lock bushings 120, 130, and 140, to master cylinder 110 and prevent rotation and disengagement.

Figure 21:
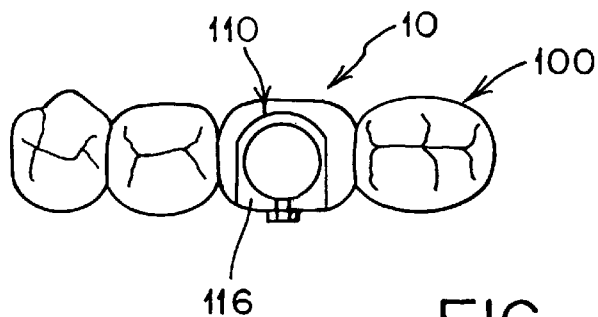
FIGS. 21 and 22 are top and side elevational views, respectively, of the surgical template shown in FIGS. 11 and 12, and the master cylinder shown in FIGS. 13 and 14, forming a surgical template assembly.
Figure 22:
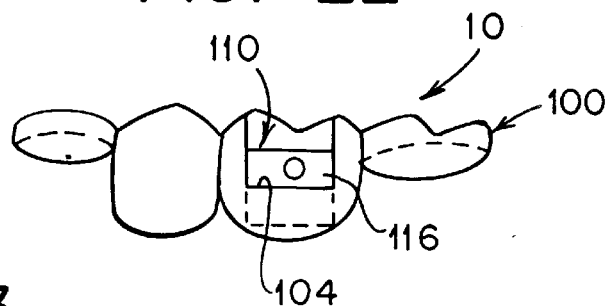

With reference now to FIGS. 21 and 22, cutout 104 of surgical template 100 receives outwardly extending flange 116 of master cylinder 110 when master cylinder 110 is placed into hole 102 in surgical template 100 thereby forming surgical template 10. In particular, flange 116 of master cylinder 110 is designed to prevent rotation, and thus, prevent master cylinder 110 from unseating or spinning during the dental implant drilling procedure. From the present description, it will be appreciated to those skilled in the art that fiducial markers 70, having served their function of providing positional coordination between the CT scan data, the computer-driven milling machine, and the computer-generated simulated dental implant, can be removed after hole 102 (FIG. 11) has been drilled, and thus, are not shown FIGS. 21–29.

Figure 23:
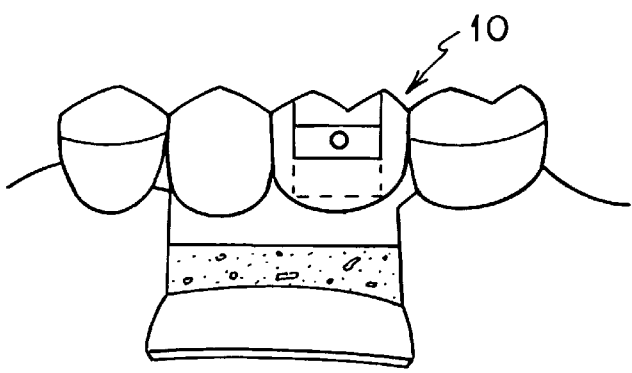
FIG. 23 is a side elevational view of the surgical template assembly shown in FIG. 22 in position over a patient's jawbone with the gum opened.
Figure 24:
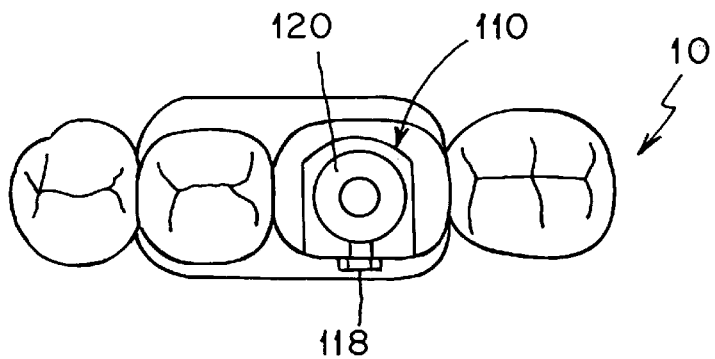
FIG. 24 is a top view of the surgical template assembly shown in FIG. 21 with the first drill bushing shown in FIG. 16.

FIGS. 23–28 illustrate the procedure of installing a dental implant in a patient's jawbone using surgical template assembly 10. First, the patient's gum is opened and surgical template assembly 10 is attached to the patient's teeth, as shown in FIG. 23. From the present description, it will be appreciated to those skilled in the art that surgical template assembly 10 can be placed on top of the gums, the teeth and/or previously installed implants.

Figure 25:
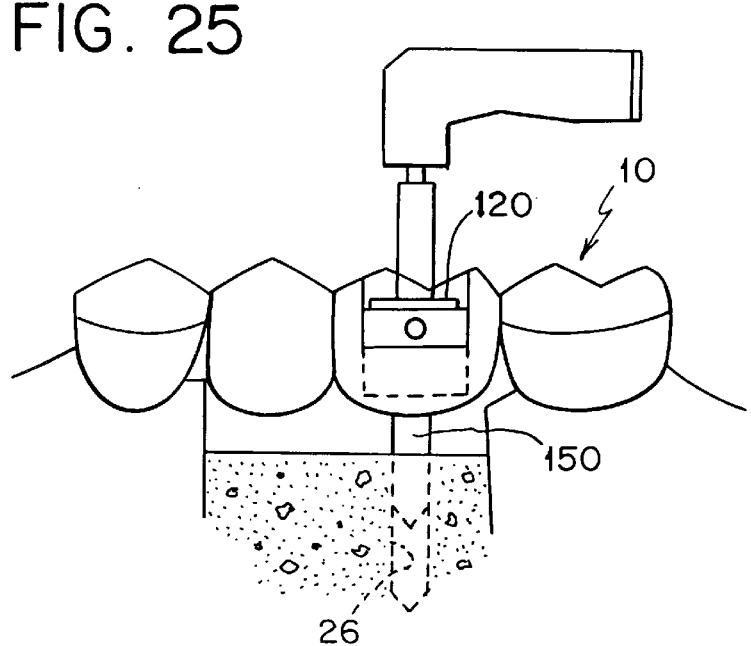
FIG. 25 is a side elevational view of the surgical template assembly shown in FIG. 24 guiding a drill bit for drilling a pilot hole in the patient's jawbone.
Figure 26:
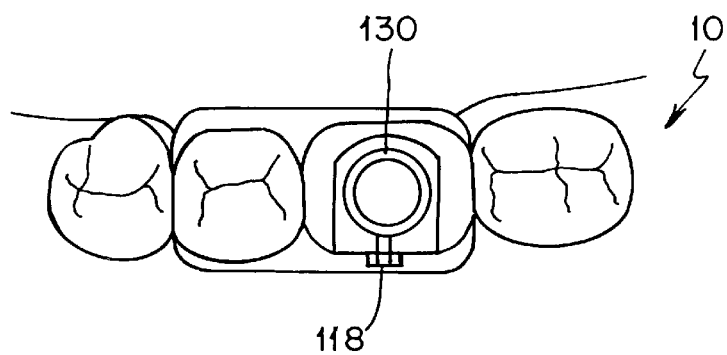
FIG. 26 is a top view of the surgical template assembly shown in FIG. 21 with the second drill bushing shown in FIG. 18.

Next, first drill bushing 120 is secured in master cylinder 110 by setscrew 118 (FIG. 24) and a surgeon guides a drill bit 150 to form a pilot hole 26 in the patient's jawbone (FIG. 25). First drill bushing 120 is then removed, and second drill bushing 130 having a larger diameter axial bore compared to first drill bushing 120 is inserted in master cylinder 110 and secured with setscrew 118 (FIG. 26). The surgeon performs a second drilling operation with a drill bit 160 to enlarge hole 26 to a properly sized hole 28 for receiving a dental implant (FIG. 27). FIG. 28 illustrates a dental implant 170 inserted and guided by implant bushing 140 in master cylinder 110 and secured to the patient's jawbone. From the present description, it will be appreciated to those skilled in the art that the dental implant can be a screw-type dental implant, a press-fit dental implant, or combination thereof. Alternatively, a separate countersinking drill, other drills or burs, or a bone tap can be used which is guided by a bushing prior to installing the dental implant.

From the present description it will also be appreciated to those skilled in the art that the various bushings allow the drill bits and implants to pass through them while at the same time rigidly holding each of them in the same fixed trajectory to precisely cut a hole and install the dental implant into the patient's jawbone to match the computer-generated simulation of the dental implant previously performed.

While only one master cylinder and two different sized drill bushings are shown, it will be appreciated to those skilled in the art that various bushings can be utilized for guiding drills, punches, taps, and implants, e.g., a round bur bushing, an initial 2-mm bushing, a soft-tissue punch bushing, a 3-mm bushing, a bone tape bushing, countersink bushing, and a dental implant bushing.

While the illustrated embodiment of surgical template assembly 10 is described with reference to implanting one dental implant, it will be appreciated to those skilled in the art that a surgical template assembly and method can be applied to the installation of several implants, e.g., a surgical template in the form of an arch corresponding to the jawbone of a patient.

Figure 29:
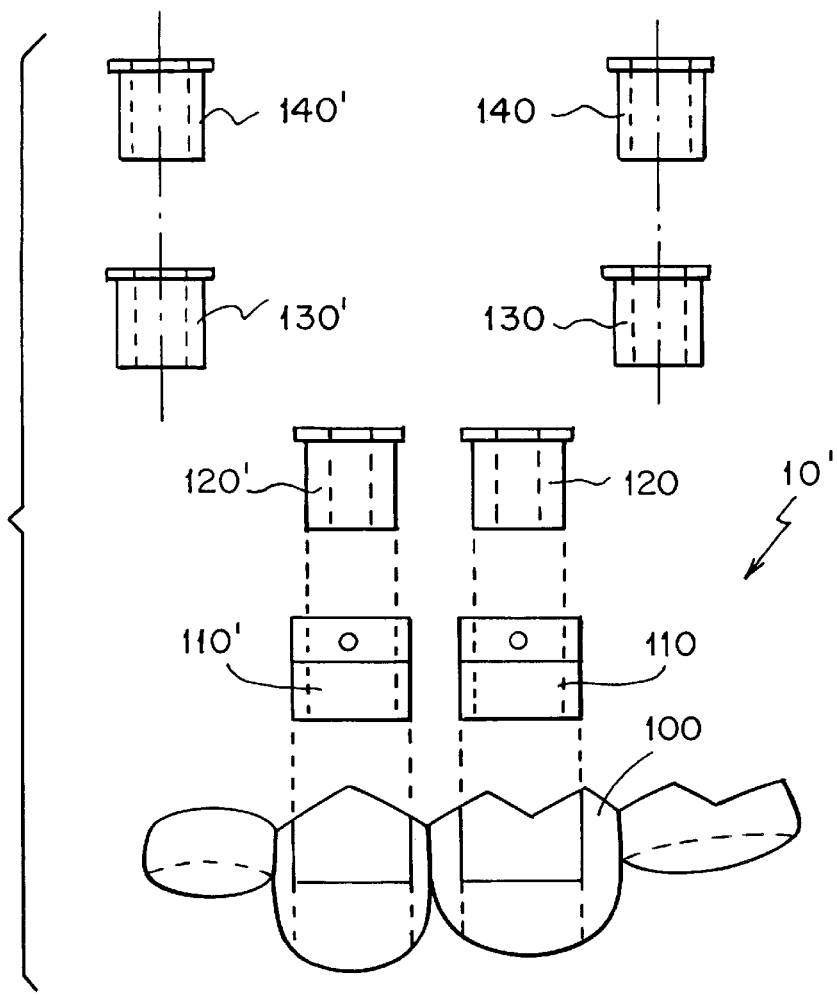
FIG. 29 is an exploded side elevational view of another embodiment of a novel surgical template assembly according to the present invention for drilling and guiding two dental implants.

For example, FIG. 29 shows an alternative embodiment of a surgical template assembly 10' for locating and surgically implanting two dental implants, e.g., dental implants corresponding to simulated dental implants 4 and 5 in FIG. 9. Surgical template assembly 10' is similar to surgical template 10 with the addition of a second set of components comprising a master cylinder 110' and bushings 120', 130', and 140'. It will be appreciated that a surgical template assembly can accommodate any number of implants, e.g., for installing ten dental implants along the arch of a patient's jawbone and include a number of interchangeable components.

As described and illustrated, surgical template assembly 10 and 10' guide various sized drill bits as well as the dental implant itself. This results in the dental implant(s) being placed where the dental implant(s) simulation dictates.

From the present description it will be appreciated that the present invention provides:
   (a) a method of transferring CT data to a computer-driven milling machine for precisely locating the drill and dental implant guides in a surgical template;
   (b) a component system to rigidly hold and guide various drill bits and the dental implant during surgery; and (c) a method of using a surgical template assembly designed from the start with tooth orientation and dental implant positioning based on CT scan data of the patient's jawbone and computer-generated simulation of the dental implant by interfacing with a computer-driven milling machine, and which comprises a component system which ensures precision dental implant surgery.

From the present description, it will also be appreciated by those skilled in the art that a dental surgeon can obtain and make a plastic replica of the teeth that a patient is missing. The surgeon can then send the plastic replica to a radiological laboratory where the laboratory attaches fiducial markers to the plastic replica to form a CT scan appliance and takes a CT scan of the patient wearing the CT scan appliance. The CT scan data can then be transferred to the surgeon wherein using a software program the location of a simulated dental implant can be determined. Alternatively, the laboratory can also determine the location of a simulated dental implant. The computer-generated simulated dental implant data can then be sent to a machine shop, where via interfacing with a computer-driven milling machine, a hole can be located in the CT scan appliance to form a surgical template. The surgical template can then be returned to the dental surgeon for locating and installing a dental implant in the patient as explained above.

Thus, while only several embodiments of the present invention have been illustrated and described, it will be appreciated to those skilled in the art that many changes and modifications may be made thereunto, without departing from the spirit and scope of the invention.

What is claimed is:

1. A method for locating a dental implant in a patient's jawbone, said method comprising the steps of:

fitting a CT scan appliance to a patient's mouth, said CT scan appliance having at least one radiopaque fiducial marker;

obtaining CT scan data of the patient's jawbone and said CT scan appliance;

computer generating an image of the patient's jawbone from said CT scan data and a simulation of a dental implant; and providing a computer-driven milling machine having a table including tooling locators and holes for locating said CT scan appliance;

coordinating said CT scan appliance to said computer driven milling machine, said fiducial marker providing coordination between said CT scan data, said computer generated simulation of said dental implant and said computer driven milling machine;

supporting said CT scan appliance on said computer-driven milling table;

coordinating said CT scan appliance to said computer driven milling machine;

drilling, via said computer-driven milling machine, a hole in said CT scan appliance to form a surgical template, said computer-driven milling machine being interfaced with said computer-generated simulation of said dental implant so that when said surgical template is refitted in the patient's mouth, a trajectory of said hole into the patient's jawbone corresponds to a trajectory of said computer-generated simulation of said dental implant into said computer-generated image of the patient's jawbone;

fitting said surgical template to the patient's mouth; and guiding a drill through said hole in said surgical template and into the patient's jawbone to form a hole in the patient's jawbone.

2. The method according to claim 1, wherein said CT scan appliance comprises three radiopaque fiducial markers, said radiopaque fiducial markers providing coordination between said CT scan data, said computer-generated simulation of said dental implant, and said computer-driven milling machine.

3. The method according to claim 1, wherein said step of guiding a drill through said hole in said surgical template comprises inserting a drill bushing in said hole for guiding said drill.

4. The method according to claim 3, wherein said step of guiding a drill through said hole in said surgical template comprises inserting a master cylinder in said hole in said surgical template and inserting a drill bushing in said master cylinder to form a surgical template assembly.

5. The method according to claim 1, further comprising the step of guiding a dental implant into said hole in said surgical template and into said hole in the patient's jawbone.

6. The method according to claim 5, wherein the step of guiding a dental implant comprises the steps of inserting a master cylinder in said hole in said surgical template and inserting an implant bushing in said master cylinder for guiding said dental implant into said hole in the patient's jawbone.

7. A method for locating a dental implant in a patient's jawbone, said method comprising the steps of:

providing a replica of prospective teeth to be supported by a dental implant;

providing a computer-driven milling machine having a table including tooling locators and holes for locating a CT scan appliance;

securing said replica to said table;

securing at least one radiopaque fiducial marker to said replica to form a CT scan appliance;

coordinating said at least one radiopaque fiducial marker to said computer-driven milling machine, said fiducial marker providing coordination between said CT scan data, said computer generated simulation of said dental implant and said computer driven milling machine; and positioning said CT scan appliance in a patient's mouth;

obtaining CT scan data of the patient's jawbone and said at least one fiducial marker;

computer generating an image of the patient's jawbone from said CT scan data and a superimposed simulation of a dental implant;

re-supporting said CT scan appliance to said table in said computer-driven milling machine;

drilling, via said computer-driven milling machine, a hole in said CT scan appliance to form a surgical template, said computer-driven milling machine being interfaced with said computer-generated simulation of said dental implant so that when said surgical template is refitted in the patient's mouth, a trajectory of said hole in said surgical template into the patient's jawbone corresponds to a trajectory of said computer-generated simulation of said dental implant into said computer-generated image of the patient's jawbone, said at least one fiducial marker providing positional coordination between said CT scan data, said computer-generated dental implant position, and said computer-driven milling machine;

inserting a master cylinder in said hole in said surgical template;

inserting a drill bushing in said master cylinder to form a surgical template assembly;

positioning said surgical template assembly in the patient's mouth;

guiding a drill through said drill bushing in said surgical template assembly to provide a hole in the patient's jawbone.

8. The method according to claim 7, further comprising the steps of removing said drill bushing and inserting an implant bushing in said master cylinder, and guiding a dental implant through said implant bushing in said master cylinder in said surgical template and into said hole in the patient's jawbone.

9. The method according to claim 7, wherein said replica provides final tooth position.

10. The method according to claim 7, wherein said replica comprises plastic.

11. A method for fabricating a surgical template for use in locating a dental implant in a patient's jawbone, said method comprising the steps of:

obtaining a CT scan appliance having at least one radiopaque fiducial marker;

obtaining computer-generated data of the CT scan appliance and jawbone and a computer generating simulation of a dental implant;

supporting said CT scan appliance in a computer-driven milling machine having a table including tooling locators and holes for locating said CT scan appliance; and coordinating said CT scan appliance to said computer-driven milling machine, said fiducial marker providing coordination between said CT scan data, said computer-generated simulation of said dental implant and said computer driven milling machine; and drilling, via said computer-driven milling machine, a hole in said CT scan appliance to form a surgical template, said computer-driven milling machine being interfaced with said computer-generated simulation of said dental implant so that when said surgical template is refitted in the patient's mouth, a trajectory of said hole in said CT scan appliance into the patient's jawbone corresponds to a trajectory of said computer-generated simulation of said dental implant into said computer-generated image of the patient's jawbone.

12. A surgical template positionable in a mouth of a patient for use in locating a dental implant in a patient's jawbone, said surgical template comprising:

a replica of prospective teeth to be implanted comprising a hole therethrough drilled by a computer-driven milling machine interfaced with a computer-generated image of a patient's jawbone and a computer-generated simulation of a dental implant so that, when said surgical template is placed in the patient's mouth, a trajectory of said hole in said replica into the patient's jawbone corresponds to a trajectory of said computer-generated simulation of said dental implant into said computer-generated image of the patient's jawbone, said replica including at least one radiopaque, hollow fiducial marker having a conically-shaped upper portion.

13. The surgical template according to claim 12, further comprising at least one drill bushing releasably insertable in said hole in said replica for guiding a drill.

14. The surgical template according to claim 13, further comprising a master cylinder insertable in said hole in said surgical template and in which is receivable said at least one drill bushing.

15. The surgical template according to claim 14, further comprising an implant bushing releasably insertable in said master cylinder for guiding a dental implant.

16. The surgical template according to claim 12, wherein said replica comprises three fiducial markers.

17. The surgical template according to claim 12, wherein said replica comprises plastic.

18. The surgical template according to claim 12, wherein said replica comprises at least one anchor for attaching to the patient's teeth.

19. The surgical template according to claim 12, wherein said replica comprises a plurality of holes therethrough drilled by a computer-driven milling machine interfaced with a computer-generated image of a patient's jawbone and a computer-generated simulation of a plurality of dental implants so that, when said surgical template is placed in the patient's mouth, trajectories of said plurality of holes into the patient's jawbone correspond to trajectories of said computer-generated simulation of said plurality of said simulated dental implants into said computer-generated image of the patient's jawbone.

20. The surgical template according to claim 19, further comprising a plurality of master cylinders each insertable in one of said plurality of holes in said surgical template, a plurality of drill bushings each releasably insertable in one of said plurality of implant cylinders for guiding at least one drill, and a plurality of master bushings releasably insertable in said master cylinder for guiding a plurality of dental implants.

* * * * *